(12) United States Patent
Matov et al.

(10) Patent No.: US 11,417,431 B2
(45) Date of Patent: Aug. 16, 2022

(54) VIRTUALLY TESTING FORCE PLACED ON A TOOTH

(71) Applicant: Align Technology, Inc., San Jose, CA (US)

(72) Inventors: Vadim Matov, San Jose, CA (US); Sergei Brodsky, San Jose, CA (US); Fuming Wu, Pleasanton, CA (US)

(73) Assignee: Align Technology, Inc., San Jose, CA (US)

( * ) Notice: Subject to any disclaimer, the term of this patent is extended or adjusted under 35 U.S.C. 154(b) by 1085 days.

(21) Appl. No.: 15/789,798

(22) Filed: Oct. 20, 2017

(65) Prior Publication Data

US 2018/0039755 A1 Feb. 8, 2018

Related U.S. Application Data

(63) Continuation of application No. 13/365,117, filed on Feb. 2, 2012, now abandoned.

(51) Int. Cl.
*G16H 50/50* (2018.01)
(52) U.S. Cl.
CPC .................................. *G16H 50/50* (2018.01)
(58) Field of Classification Search
None
See application file for complete search history.

(56) References Cited

U.S. PATENT DOCUMENTS

| | | | |
|---|---|---|---|
| 5,879,158 A | 3/1999 | Doyle et al. | |
| 6,227,850 B1 * | 5/2001 | Chishti | A61C 7/00 433/24 |
| 6,471,511 B1 | 10/2002 | Chishti et al. | |
| 6,682,346 B2 | 1/2004 | Chishti et al. | |
| 6,802,713 B1 | 10/2004 | Chishti et al. | |
| 7,320,592 B2 | 1/2008 | Chishti et al. | |
| 7,543,511 B2 | 6/2009 | Kimura et al. | |
| 7,841,858 B2 | 11/2010 | Knopp et al. | |
| 7,874,837 B2 | 1/2011 | Chishti et al. | |
| 8,439,672 B2 * | 5/2013 | Matov | A61B 6/14 433/24 |
| 2006/0223022 A1 | 10/2006 | Solomon | |
| 2006/0257815 A1 | 11/2006 | De Dominicis | |
| 2008/0109198 A1 * | 5/2008 | Knopp | A61C 7/08 703/11 |
| 2008/0268400 A1 | 10/2008 | Moss et al. | |
| 2009/0030347 A1 | 1/2009 | Cao | |
| 2009/0191502 A1 | 7/2009 | Cao et al. | |
| 2009/0191503 A1 | 7/2009 | Matov et al. | |
| 2010/0138025 A1 | 6/2010 | Morton et al. | |
| 2010/0280798 A1 * | 11/2010 | Pattijn | A61C 7/002 703/1 |
| 2013/0204599 A1 | 8/2013 | Matov et al. | |

* cited by examiner

*Primary Examiner* — Michael L Borin
(74) *Attorney, Agent, or Firm* — Shay Glenn LLP

(57) ABSTRACT

Embodiments of the present disclosure include computing device related, system, and method embodiments for virtually testing force placed on a tooth are described herein. One method embodiment includes receiving initial orthodontic data (IOD) of teeth, and receiving a desired position of a tooth contained in the IOD. The method embodiment can also include computing a desired force and torque to be applied to the tooth to reach the desired position, wherein the force and torque are applied using a dental attachment. The method embodiment can include virtually testing and adjusting the attachment iteratively to reach the desired force and torque, and displaying the force and torque applied to the tooth via a user interface.

12 Claims, 5 Drawing Sheets

VIRTUALLY TESTING FORCE PLACED ON A TOOTH

PRIORITY INFORMATION

This application is a continuation of U.S. application Ser. No. 13/365,117, filed Feb. 2, 2012, the entire contents of which are hereby incorporated by reference.

TECHNICAL FIELD

The present disclosure relates to systems and methods for virtually testing force placed on a tooth.

BACKGROUND

The present disclosure relates generally to the field of dental treatment. More specifically the present disclosure relates to virtually testing force placed on a tooth.

Many dental treatments involve repositioning misaligned teeth and changing bite configurations for improved cosmetic appearance and dental function. Orthodontic repositioning can be accomplished, for example, by applying controlled forces to one or more teeth over a period of time.

An example of orthodontic repositioning that can occur through a dental process that uses one or more positioning appliances for realigning teeth. Placement of an appliance over the teeth can provide controlled forces in specific locations to gradually move the teeth into a new configuration. Repetition of this process with successive appliances in progressive configurations can move the teeth through a series of intermediate arrangements to a final desired arrangement.

Appliances, or attachments, can have an already designed shape. An attachment may be placed on a patient's tooth with the theory that the attachment will act on the tooth to move it in a particular direction. However, this treatment plan is typically selected by a treatment professional based upon the treatment professional's experience with the type of attachment. However, the actual result based on the actual forces at work may result in a different orientation than expected. This may result in providing more, less, or different movement to achieve the desired result than was initially predicted by the treatment professional.

DETAILED DESCRIPTION

Figure 1A:
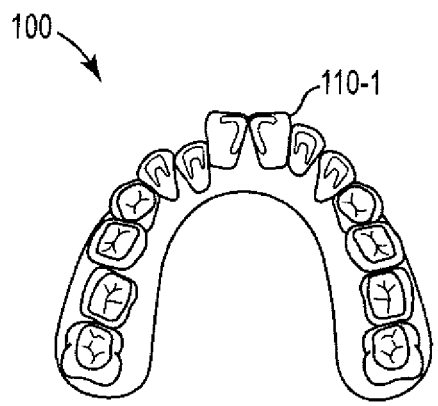
FIG. 1A illustrates a virtual initial dental model according to one or more embodiments of the present disclosure.

Embodiments of the present disclosure include computing device related, system, and method embodiments for virtually testing force placed on a tooth. For example, one or more method embodiments include, receiving initial orthodontic data (IOD) of teeth, receiving a desired position of a tooth contained in the IOD, computing a desired force and torque to be applied to the tooth to reach the desired position, wherein the force and torque are applied using a dental attachment, virtually testing and adjusting the attachment iteratively to reach at least one of the desired force and torque, and displaying at least one of the force and torque applied to the tooth via a user interface.

In the following detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice a number of embodiments of this disclosure, and it is to be understood that other embodiments may be utilized and that changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. For example, 120 may reference element "20" in FIG. 1B, and a similar element may be referenced as 420 in FIG. 4.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present disclosure, and should not be taken in a limiting sense. As used herein, "a", "at least one", "a number of" something can refer to one or more such things.

Although the overarching term "orthodontics" is used herein, the present disclosure may relate to treatments of an orthognathic nature. For example, in cases including treatment of a patient's underlying skeletal structure, teeth may be rearranged by surgically repositioning underlying bones that hold the teeth in order to achieve a desired final bite arrangement. In both orthodontic and orthognathic treatment approaches, alignment of the teeth may be evaluated pre-, mid-, and/or post-treatment.

Treatment professionals typically select a treatment plan for a patient's teeth based upon experience with certain types of physical features, attachments, and/or appliances. An assumption is often made that the attachment or appliance will move the teeth or a certain tooth in a particular direction based on the shape of the attachment or appliance.

However, an actual result based on the actual forces at work may result in a different orientation than expected, which may be an undesired result. Embodiments of the present disclosure can predict the forces of a dental appliance on a particular tooth of a patient.

This can aid in understanding the forces provided by a particular attachment on a particular tooth at a particular position and/or orientation thereon, in isolation. Such information can aid in the design of the appliance and/or treatment planning, in some embodiments.

In various embodiments, with the use of computer graphic software, a treatment professional can establish a custom treatment target specific to a particular tooth of a particular patient allowing, in some embodiments, custom dental appliance design. With this treatment target in mind, a force applied to a tooth by an appliance or attachment can be virtually determined and tested.

Virtual dental models from a scan of a patient's dentition can be provided with computer-aided design and/or manufacturing systems, including tooth-treatment systems. Initial orthodontic data (IOD) representing an initial tooth arrangement may be obtained in a variety of ways. For example, the patient's teeth may be imaged to obtain digital data using direct and/or indirect structured light, X-rays, three-dimensional X-rays, lasers, destructive scanning, computer-aided tomographic images or data sets, magnetic resonance images, intra-oral scanning technology, photographic reconstruction, and/or other imaging techniques. The IOD can include an entire mouth tooth arrangement, some, but not all teeth in the mouth, and/or it can include a single tooth.

A positive model and/or negative impression of the patient's teeth or a tooth may be scanned using an X-ray, laser scanner, destructive scanner, structured light, and/or other range acquisition system to produce the IOD. The data set produced by the range acquisition system may be converted to other formats to be compatible with the software which is used for manipulating images within the data set, as described herein.

Referring now to FIG. 1A, there is illustrated a virtual initial dental model 100 according to one or more embodiments of the present disclosure. As described herein, the virtual initial dental model 100 can be obtained prior to treatment or at an intermediate state of treatment (e.g., before treatment has been completed). One or more embodiments of the present disclosure include receiving IOD and a desired position of a tooth contained in the IOD. The virtual initial dental model (e.g., derived from the IOD) can also include a model of an individual tooth (e.g., tooth 110-1) that is part of a full dental model, such as full virtual dental model 100.

Figure 1B:
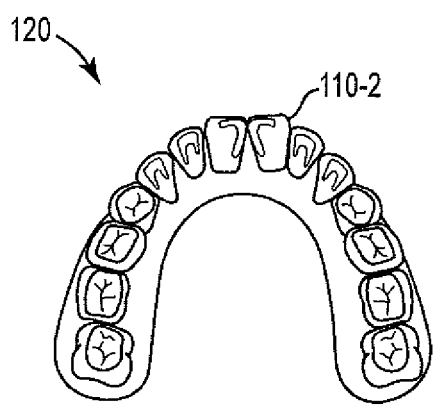
FIG. 1B illustrates a target virtual dental model corresponding to the virtual initial dental model illustrated in FIG. 1A according to the present disclosure.

FIG. 1B illustrates a target virtual dental model 120 corresponding to the virtual initial dental model illustrated in FIG. 2A according to the present disclosure. The target virtual dental model 120 can be created by modifying the virtual initial dental model 100 according to one or more treatment goals. The one or more treatment goals can be case-specific (e.g., specific to the particular patient on which the virtual initial dental model 100 was based).

In some embodiments, the target virtual dental model can reflect an intermediate tooth movement within a treatment plan. Such a tooth movement may be useful during a particular process within the treatment plan (e.g., interproximal reduction (IPR), extraction, etc.).

A target virtual dental model can also include a target model of an individual tooth (e.g., tooth 110-2) that is part of a full dental model similar to full target dental model 120. In some embodiments, the IOD and the target virtual dental model can be displayed via a user interface in three dimensions. In some embodiments for example, the presentation in three dimensions can include presenting one or more desired force and/or force movements on the models as vector arrows showing direction and/or magnitude of desired force, among other information about the force that may be helpful to the user.

In various embodiments, the force and/or torque can be based on a movement from a first position to a second position based on the use of a particular attachment. However, in some implementations, this movement can be a movement that would be achieved through use of the attachment with multiple aligners whereby a first aligner would work with the attachment to move the tooth from the first position to a second position and where a second aligner would be used with the attachment to move the tooth from the second position to a third position. Additional aligners could work with the attachment to move the tooth to other subsequent positions. In some embodiments, the forces and/or torque used to move the tooth to each of these positions could be identified and/or utilized and/or the force and/or torque from the first position to any subsequent position could be identified and/or utilized.

As discussed above, virtual testing of a force applied to a tooth by an attachment or physical feature can be utilized in the design of dental appliances for use in the mouth of a patient, such as anchors and other attachments, and potentially to aligner surfaces (e.g., dimples, ridges, thickness, etc.), materials properties, and their interaction with the teeth. Virtually testing the applied force allows a user to identify the forces present on one tooth that are provided by a particular dental appliance within a set of teeth of the mouth.

Virtually testing an applied force to a tooth can also be beneficial in determining how much force to apply to the tooth and from what one or more directions. This information can be used to determine the shape and/or positioning of the attachment to get closest to the necessary force and/or direction desired for moving the tooth.

Figure 2:
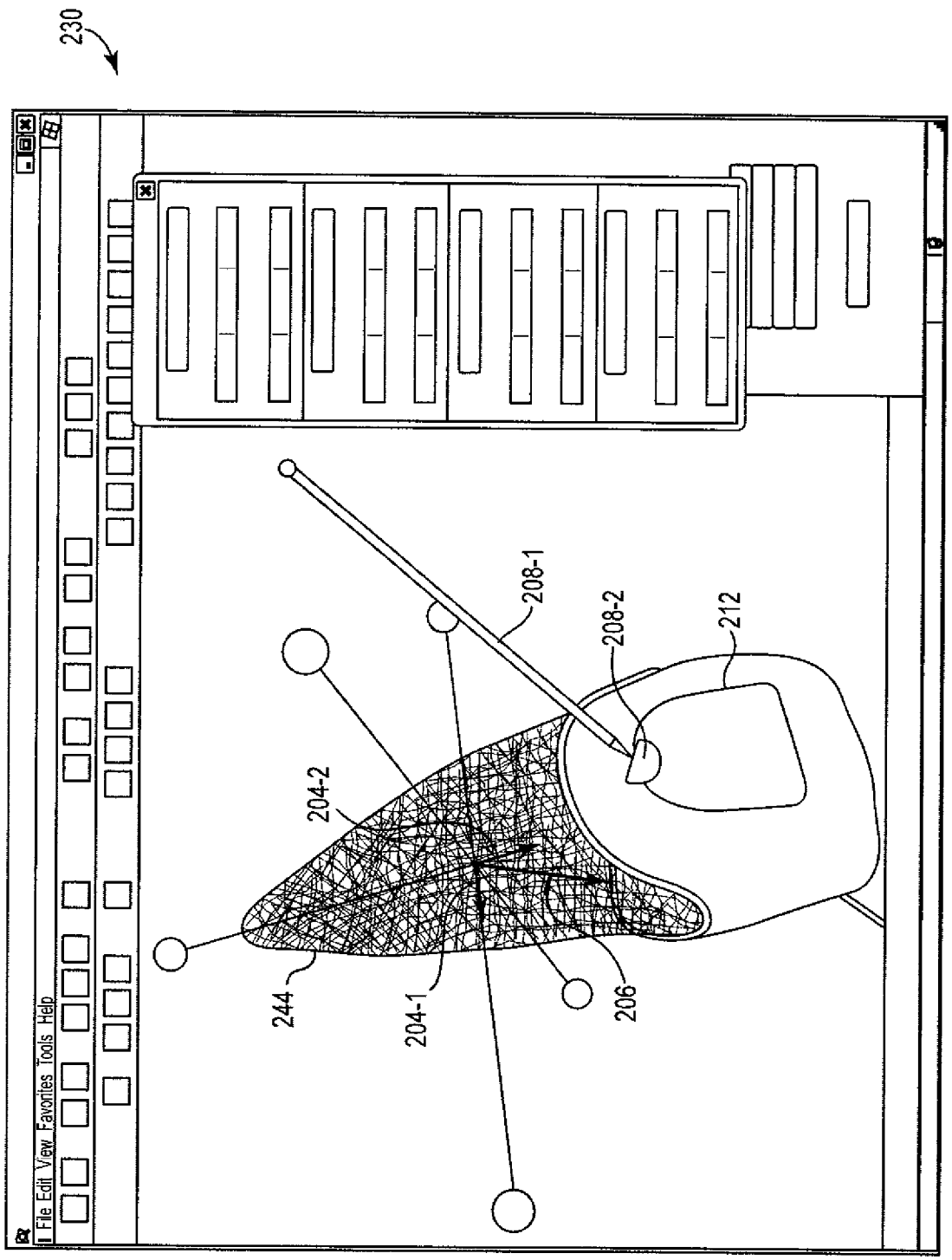
FIG. 2 illustrates an example tooth model and an exemplary user interface for testing force placed on a tooth according to one or more embodiments of the present disclosure.

FIG. 2 illustrates an example tooth model and an exemplary user interface for testing force placed on a tooth according to one or more embodiments of the present disclosure. In one or more embodiments, a user can virtually test the shape and placement of an attachment or other appliance structure (e.g., physical feature 208-2) and make adjustments to the shape and/or placement and retry the movement until the best or most satisfactory result is achieved. The model of tooth 244 includes arrows 204-1 and 204-2 representing a desired force and torque for movement of tooth 244. For example, arrows 204-1 and 204-2 can represent an ideal force and torque for movement. The model of tooth 244 includes tooth surface feature 208-2 (e.g., attachment, dimple, etc.) and an arrow 208-1 that can represent a desired feature force direction and/or magnitude, given a set of features. A feature (e.g., feature 208-2) applies a force and/or torque to the tooth 244, which can be represented by one or more arrows (e.g., arrow 206). Computing device executable instructions can also be provided, in some embodiments, to calculate an area for possible location (e.g., area 212) of a feature (e.g., feature 208-2) where the appliance can be placed on tooth 244 (e.g., for potentially best results). The tooth, as well as features of the attachment may be editable by a user (e.g., via the user interface 230), as further discussed herein.

Figure 3:
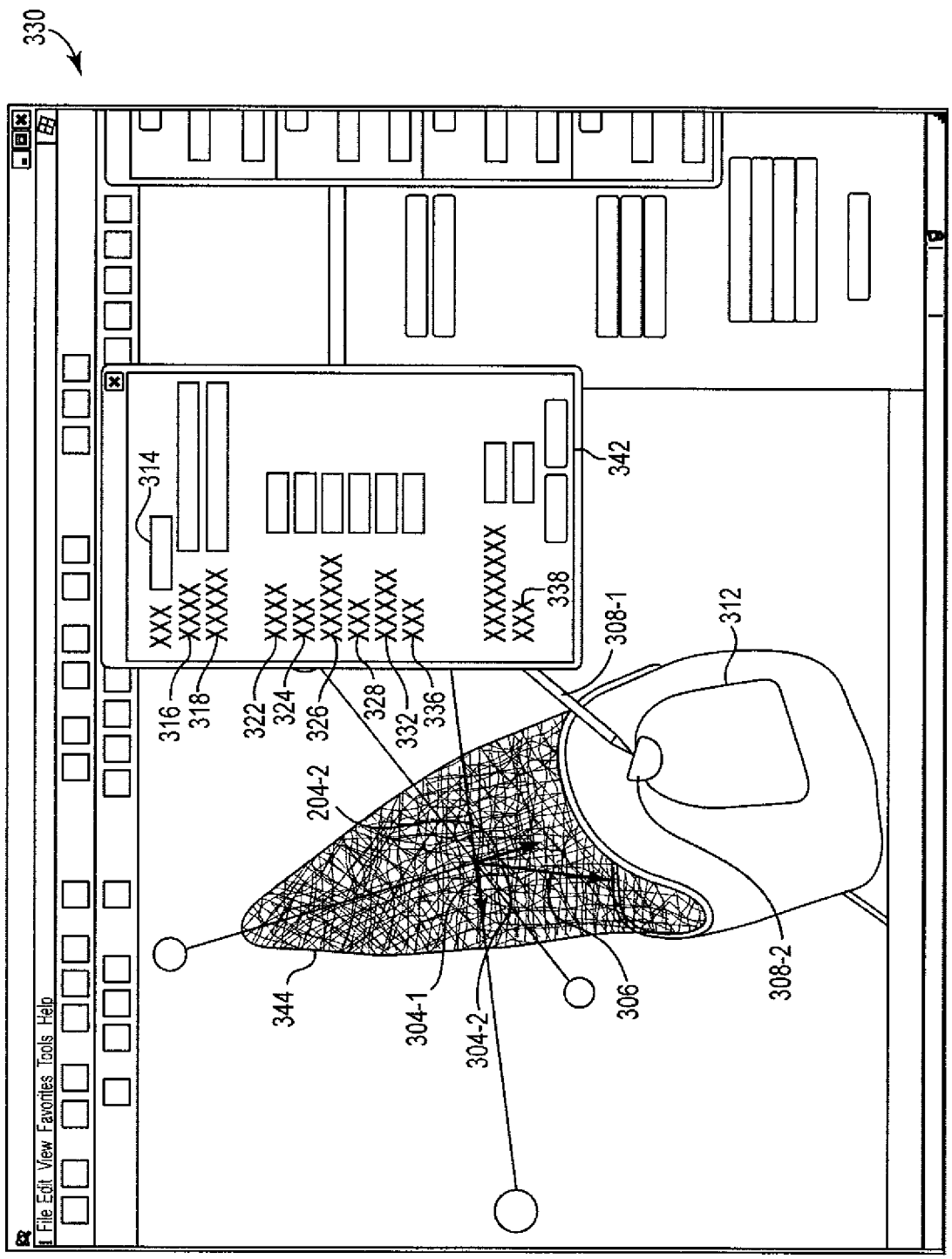
FIG. 3 illustrates an example tooth model and an exemplary user interface for testing force placed on a tooth according to one or more embodiments of the present disclosure.

FIG. 3 illustrates an example tooth model and an exemplary user interface for testing force placed on a tooth according to one or more embodiments of the present disclosure. In some embodiments a user can take data from an actual patient's mouth and determine the forces desired during a portion of a treatment plan to move a tooth from one position to another. The use of actual case data may be useful, for example where an attachment may be desired to perform a particular movement with respect to a particular tooth positioning due to a particular malocclusion. A user can enter physical parameters of an attachment (e.g., appliance, aligner, dimple, etc.) to be created into a location and orientation window 342 of user interface 330.

In various embodiments, a user can enter such parameters as a length 322, a width 324, a prominence 326, a depth 328 inside tooth 344, an activation angle 332, and/or an activator offset on inactive surfaces 334. In some embodiments, a user can also enter more advanced settings, such as an iso-surface gradient width 336 and/or a voxel size 338.

In various embodiments, a user can choose to identify tooth 344 by a number or some other identifier and enter or choose the identifier in a drop-down box such as box 314. In some embodiments, a user can also choose to enter parameters for a center of the attachment and an active surface (e.g., parameters 316 and 318).

Treatment plan case data can be analyzed to determine the movement of a particular tooth from a first position to a subsequent (e.g., desired) position. This information can then be utilized in an analysis of forces with respect to proposed attachments or other aligner related movement analysis.

In some embodiments, a user interface (e.g., model and user interface 330) is provided where a virtual model of the tooth is presented in three dimensions. Once the forces and/or moments of the forces on the tooth are determined, they can be presented on the user interface (e.g., they can be presented as vector arrows showing direction and/or magnitude of desired force and/or stress) among other information about the force that may be helpful to the user. For example, vector arrows 304-1 and 304-2 can represent desired (e.g., ideal) force and/or torque for movement of tooth 344, and vector arrow 306 can, in some embodiments, represent a force and/or torque applied to tooth 344 by a feature, such as feature 308-2. Vector arrow 308-1 can represent a desired (e.g., optimal) feature force direction and/or magnitude, given a set of features (e.g., attachment, dimple, etc.).

Tools for the creation and/or alteration of the attachments and/or other items related to the movement of the tooth can be utilized to virtually test force placed on a tooth. These tools can include one or more libraries of tooth shapes (e.g., typodonts) and/or treatment plan data (e.g., actual patient tooth data and/or other treatment planning data); attachment shapes; data regarding mounting materials that could be used; and/or data regarding other characteristics of an aligner, tooth, and/or mouth structure.

Editing tools can be provided to change the shape of the attachments and/or other items related to the movement of the tooth. For example, suitable tools could include those that are provided with respect to drafting and/or computer aided design software applications, among other tools.

In some embodiments, the desired forces and the actual forces can be illustrated on the virtual model so that the user can see the differences between the actual and desired forces (e.g., force and/or magnitude vectors for both the desired and actual forces). This can be helpful, for example, by allowing the user to see the differences and/or adjust the shape and/or position of the attachment and/or other item related to the movement of the tooth. The actual force can then be recalculated and then illustrated to show the revised force of the revised shape and/or position.

In some embodiments, multiple calculated positions and/or shapes can be illustrated (e.g., the forces generated from a first position and a second position can be illustrated together and, in some embodiments, with the desired forces). This can be beneficial, for example, to identify how the change from a first to a second position affected the forces. It can also be beneficial to identify if the change from a first to a second position is adjusting the forces created closer to those of the desired forces.

It should be noted that one force that may be quantified for movement of the tooth is for total movement of the tooth from a first position to a second position. However, forces from the gingiva and bone interactions for some force calculations can also be incorporated and, therefore, in some embodiments, forces for different stages of movement can be determined, such as initial force needed for bone breakdown versus force needed for movement once the bone breakdown has occurred. For example, in some embodiments, the movement from a first position to a second position may be determined by calculating the force sufficient to enable the tooth to begin to move (e.g., the first and second positions could be relatively close or adjacent and therefore the force to create that movement would be the force needed to begin moving the tooth).

In some embodiments, a center of mass can be calculated for the tooth, and the forces (e.g., desired forces) can be associated with the center of mass. In some embodiments, a center of resistance can be calculated, (e.g., based upon the center of mass, and/or forces such as from the gingiva and/or bone attachment) and the forces can be associated with the center of resistance.

In some embodiments, a possible placement area in which an attachment can be positioned on a tooth can be identified (e.g. area 312). This information can be obtained through experiential data programmed into the software and/or entered by the user or multiple users (e.g., using window 342). Additionally, this can be calculated based upon the forces that are to be generated.

For example, in some embodiments, the forces generated can be determined for an attachment that has been selected by the user for placement on the tooth and a possible placement area 312 can be identified for the placement of the attachment on the tooth. The possible placement area 312 can, for example, be based upon where the placement of the attachment would result in a certain result that would be within a threshold proximity to the desired result. In some embodiments, as the shape and/or orientation of the dental appliance is changed, the possible placement area can be recalculated.

The possible placement area 312 could, for instance, be based on areas where attachment could actually be achieved (e.g., portions of the tooth where an attachment would be sufficiently adhered to the tooth so that it does not come detached or obstructed by a structure such as a tooth surface not being shaped for attachment thereto or too far below the gingiva). This calculation could be determined through experiential data or based upon one or more characteristics of the tooth, and/or materials to be used (e.g., adhesion characteristics of the tooth surface, adhesion characteristics of the adhesion material, adhesion characteristics of the dental appliance material, shape of the adhesion surface of the attachment, and/or shape of the surface of the tooth, etc).

For example, the possible placement area 312 may not include the edge areas, overly curved surfaces, and/or contoured surfaces of the tooth because adhesion to those surfaces may be difficult, in some situations. It may not be reasonable to use some areas of the tooth, as certain areas would not properly associate or connect with a surface of an appliance, and as such, in some embodiments, association information and/or surface information can be used in determining possible placement areas. For example, improper association can include, for instance, an appliance position that is calculated to be undesirably close to or in contact with a neighboring tooth, an appliance position that negatively impacts a neighboring tooth and/or area surrounding the possible placement area, a position that would not provide proper fit between the attachment and another appliance such as an aligner, and/or negatively impacting the area around an aligner and/or the appliance, among others.

Improper connection with a surface of an appliance can include, for instance, can include not having a tooth surface that would provide a secure bonding surface for attachment of an appliance thereon, among others.

In some embodiments, the possible placement area 312 may by "dynamic" in that it can change as certain criteria (e.g., the shape and/or type of appliance, bonding material, material of the appliance, etc.) changes. For example, an attachment of a particular shape may have more preferable results when placed on a first area of a tooth than a second attachment having a second shape, perhaps, with a different surface shape on the surface to be bonded to the surface of the tooth and therefore, the possible placement area can be changed so that the user interface can indicate the changes to a user.

Figure 4:
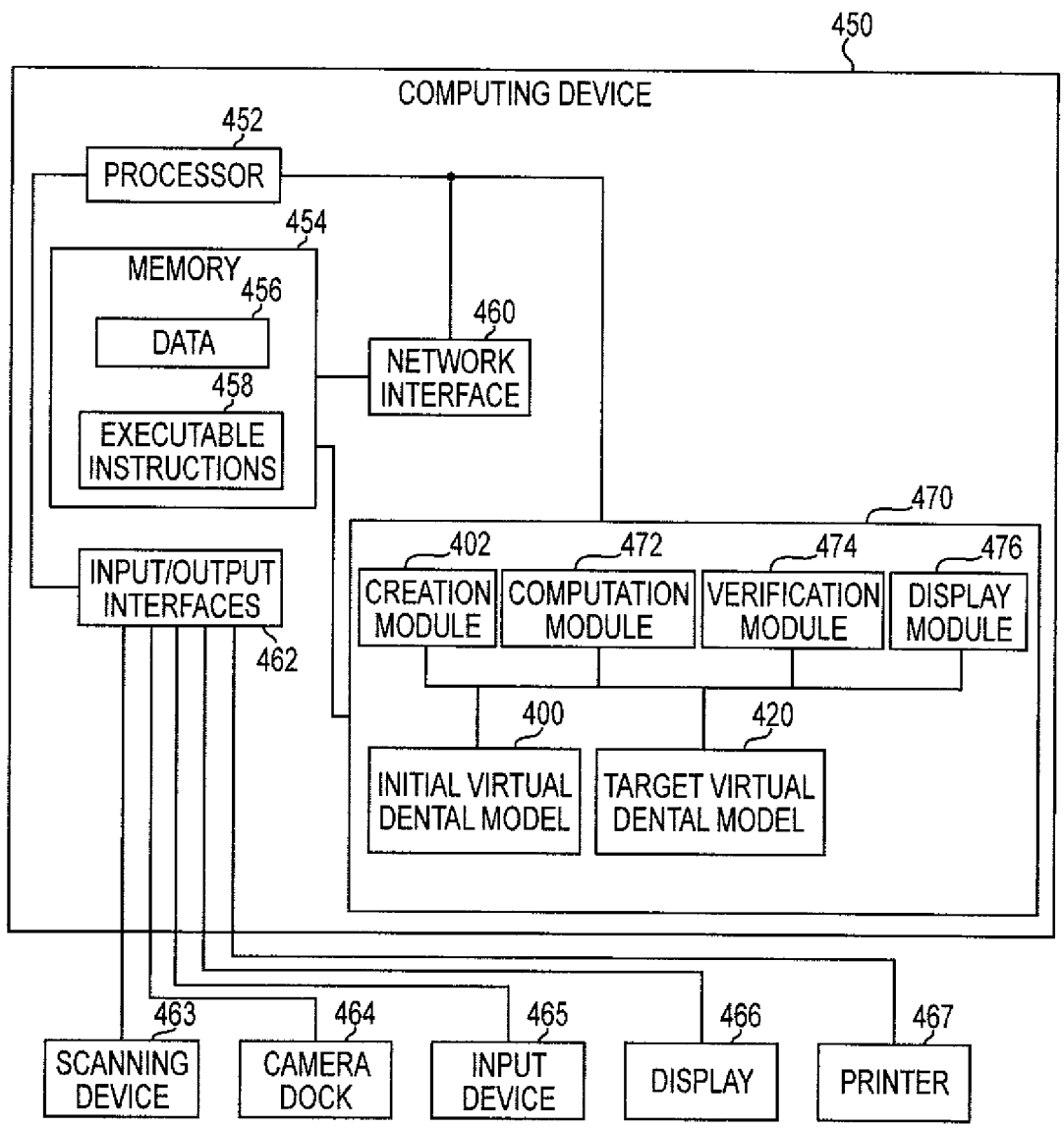
FIG. 4 illustrates a system for virtually testing force placed on a tooth according to one or more embodiments of the present disclosure.

FIG. 4 illustrates a system for virtually testing force placed on a tooth according to one or more embodiments of the present disclosure. In the system illustrated in FIG. 4, the system includes a computing device 450 having a number of components coupled thereto. The computing device 450 includes a processor 452 and memory 454. The memory can include various types of information including data 456 and executable instructions 458, as discussed herein.

Memory and/or the processor may be located on the computing device 450 or off the device, in some embodiments. As such, as illustrated in the embodiment of FIG. 4, a system can include a network interface 460. Such an interface can allow for processing on another networked computing device, can be used to obtain information about the patient, and/or can be used to obtain data and/or executable instructions for use with various embodiments provided herein.

As illustrated in the embodiment of FIG. 4, a system can include one or more input and/or output interfaces 462. Such interfaces can be used to connect the computing device with one or more input and/or output devices.

For example, in the embodiment illustrated in FIG. 4, the system can include connectivity to a scanning device 463, a camera dock 464, an input device 465 (e.g., a keyboard, mouse, etc.), a display device 466 (e.g., a monitor), a printer 467, and/or one or more input devices 465. The input/output interfaces 462 can receive executable instructions and/or data, storable in the data storage device (e.g., memory 454), representing a digital dental model of a patient's dentition.

In some embodiments, the scanning device 463 can be configured to scan one or more physical molds of a patient's dentition. In one or more embodiments, the scanning device 463 can be configured to scan the patient's dentition directly. The scanning device 463 can be configured to input data into the computing device wherein the data can be provided to the application modules 470.

The camera dock 464 can receive an input from an imaging device (e.g., a two-dimensional or three dimensional imaging device) such as a digital camera, a printed photograph scanner, intra-oral scanner, or other suitable imaging device. The input from the imaging device can, for example, be stored in the data storage device (e.g., memory 454).

The processor 452 can be configured to provide a visual indication of a virtual dental model on the display 466 (e.g., on a graphical user interface (GUI) running on the processor 452 and visible on the display 466). The GUI can be configured to allow a treatment professional or other user to input treatment goals, to create a target virtual dental model 420, and/or enter desired or actual attachment parameters. Input received via the GUI can be sent to the processor 452 as data and/or can be stored in memory 454.

Such connectivity can allow for the input and/or output of data and/or instructions among other types of information. Although some embodiments may be distributed among various computing devices within one or more networks, such systems as illustrated in FIG. 4, can be beneficial in allowing for the capture, calculation, and/or analysis of information discussed herein.

The processor 452, in association with the data storage device (e.g., memory 454), can be associated with data and/or application modules 470. The processor 452, in association with the memory 454, can store and/or utilize data and/or execute instructions to provide a number of application modules for virtually testing force placed on a tooth. As used herein, a module can be a stand alone program or portion of a program or can be a set of code that provides a particular functionality and may not be stand alone and may not even include instructions interspersed within a set of code.

Such data can include the virtual initial dental model 400 and/or the target virtual dental model 420. Such application modules can include a computation module 472, a verification module 474, a creation module 402, and/or a display module 476.

The computation module 472 can, for example, be configured to compute a desired position, a desired orientation, and/or a desired relative magnitude of point contact force of an attachment to achieve the target virtual dental model 420. The creation module 402 can be configured to virtually create an attachment, and the verification module 474 can be configured to test the virtually created attachment and/or verify it has the desired position, orientation, and relative magnitude of point contact force. The display module 476 can be configured to display the virtually created attachment and/or the point contact force. The display module 476 can be configured to display the information on display device 466.

Figure 5:
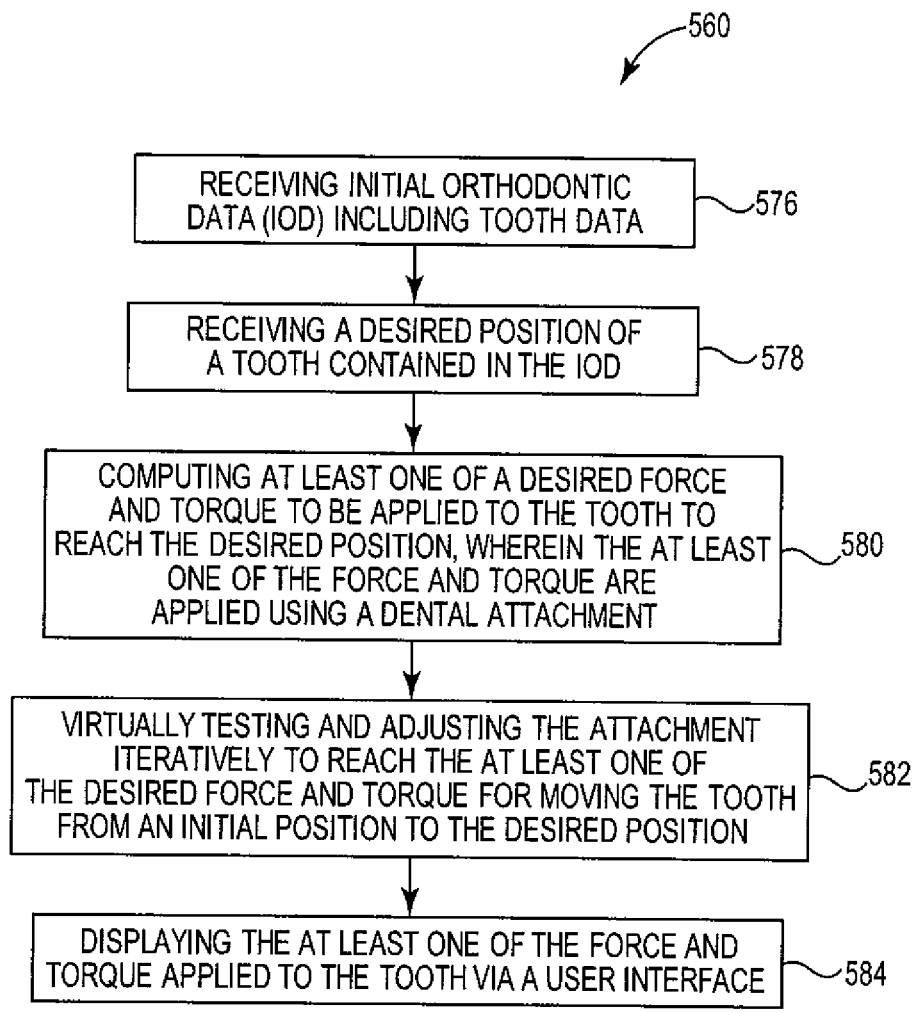
FIG. 5 illustrates a method for testing force placed on a tooth according to one or more embodiments of the present disclosure.

FIG. 5 illustrates a method for testing force placed on a tooth according to one or more embodiments of the present disclosure. At 576, initial orthodontic data (IOD) of teeth, including teeth data, is received.

The IOD may be received in a variety of ways and may contain a variety of information. For example, the IOD can include one or more of an initial single tooth model, an initial teeth set model, a gum structure, and/or a mouth bone structure.

The patient's teeth may be imaged to obtain digital data using direct and/or indirect structured light, X-rays, three-dimensional X-rays, lasers, destructive scanning, computer-aided tomographic images and/or data sets, magnetic resonance images, intra-oral scanning technology, photographic reconstruction, and/or other imaging techniques. The IOD can include any portion of the mouth, from an entire mouth tooth arrangement to a single tooth.

A positive model and/or negative impression of the patient's teeth or a tooth may be scanned using an X-ray, laser scanner, destructive scanner, structured light, and/or other scanning system to produce data for the IOD. In some embodiments, the data set produced by the scanning system may be converted to other formats to be compatible with the software which is used for manipulating images within the data set.

A desired position of a tooth contained in the IOD is received at 578. The desired position may be the choice of a treatment professional and/or the patient. The desired position can also be a position that has been used for previous patients with similar teeth positioning. In some embodiments, the desired position may be the same as an initial position (e.g., the tooth is to stay anchored in the same position as one or more other teeth move).

At 580, at least one of a desired force and torque to be applied to the tooth in order to reach the desired position is computed. The at least one of a desired force and torque can be applied using a dental attachment (e.g., appliance, dimple, anchor, etc.).

Using this desired force and/or torque, an attachment can be virtually created using a number of aforementioned creation tools, which include editing tools to change the shape of the attachments or other items related to the movement of the tooth. The attachment can be virtually tested and adjusted iteratively at 582 until at least one of the desired force and torque is reached.

In some embodiments, virtually testing and adjusting the attachment can include virtually testing and adjusting the attachment iteratively to reach at least one of the desired force and torque for moving the tooth from an initial position to the desired position.

In various embodiments, where anchoring of a tooth is desired virtually testing and adjusting the attachment can include virtually testing and adjusting the attachment iteratively to reach at least one of the desired force and torque for maintaining the tooth in an initial position and a desired position that are the same.

In some embodiments, an actual force generated by an attachment chosen by a patient, treatment professional, and/or other user can be determined and/or estimated. Based on this actual force, an area for the placement of the attachment on the tooth can be chosen.

The area for the placement of the attachment on the tooth can also be determined without the actual force determination. For example, the desired force and/or torque to be applied to the tooth can be compared to the determined actual force, and the results can, for instance, be presented to a user via a user interface. This can be helpful, for example, by allowing the user to see differences and adjust the shape and/or position of the attachment or other dental appliance related to the movement of the tooth.

In some embodiments, the force can then be recalculated and illustrated to show a revised force of the revised shape and/or position. For example, the desired position, desired orientation, and/or desired relative magnitude of point contact force can be recomputed with a new constraint if the attachment does not reach the desired outcome, treatment goal, and/or model. In various embodiments, the attachment can be recreated with a different shape if desired outcomes are not met.

At 584, the at least one of the force and torque applied to the tooth can be displayed via a user interface. Once the forces and/or moments of the forces on the tooth are determined, they can be presented on the user interface (e.g., they can be presented as vector arrows showing direction and/or magnitude of desired force) among other information about the force that may be helpful to the user.

Virtually testing force placed on a tooth can be beneficial for many reasons, including the utilization of real world force information, tooth data, and/or other structural data to calculate the position for placement and/or potential shape of an attachment or other appliance feature without actually having to test all of these iterations in an actual patient or group of patients. The results can include more accurate movement of teeth, thereby reducing the time of treatment and/or increasing patient satisfaction, among others.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. A method of forming dental appliances based on virtually testing force placed on a virtual tooth, the method comprising:

receiving and a desired position of a tooth of a patient included in initial orthodontic data (IOD), wherein the IOD includes tooth data of the patient;

determining at least one of a desired force and torque to be applied to the virtual tooth such that the virtual tooth moves from an initial position to the desired position;

determining a placement area on the virtual tooth for a virtual dental attachment to achieve a result within a threshold proximity to at least one of the desired force and torque applied to the virtual tooth in response to interaction between a virtual aligner and the virtual dental attachment;

determining an attachment location in the placement area on the virtual tooth for the virtual dental attachment;

displaying, via a user interface, the virtual dental attachment at the attachment location on the virtual tooth;

receiving instructions from a user to adjust the attachment location of the virtual dental attachment in the placement area iteratively to reach the at least one of the desired force and torque applied by the virtual aligner and the virtual dental attachment to reach a final attachment location of the virtual dental attachment to move the virtual tooth from the initial position to the desired position; and creating an aligner and a dental attachment shaped in accordance with the virtual aligner and virtual dental attachment, the aligner and the dental attachment shaped to cooperate together to apply the at least one of the desired force and torque to the tooth of the patient when the dental attachment is positioned at the final attachment location on the tooth of the patient.

2. The method of claim 1, wherein determining the at least one of the desired force and torque applied to the virtual tooth by the virtual aligner and the virtual dental attachment includes determining an initial force to cause bone breakdown of the tooth.

3. The method of claim 1, wherein the method includes virtually testing and virtually adjusting the attachment location in the placement area to reach an attachment location of the virtual dental attachment to move the virtual tooth from the initial position to a position within a threshold proximity to the desired position.

4. The method of claim 1, wherein determining the placement area for the virtual dental attachment includes ignoring areas of the virtual tooth in which the virtual dental attachment would not adhere to the virtual tooth.

5. The method of claim 1, wherein determining the placement area on the virtual tooth includes determining the placement area on the virtual tooth based on the at least one of the desired force and torque to be applied to the virtual tooth.

6. The method of claim 1, wherein determining the placement area on the tooth includes determining the placement area on the tooth based on a center of resistance of the tooth associated with the at least one of the desired force and torque to be applied to the tooth.

7. The method of claim 1, wherein the method includes virtually testing and virtually adjusting the attachment location in the placement area iteratively to reach the at least one of the desired force and torque to reach an attachment location of the virtual dental attachment to move the virtual tooth by an intermediate tooth movement from the initial position to the desired position for a portion of a treatment plan.

8. The method of claim 1, wherein determining the placement area on the virtual tooth includes determining whether a surface of the virtual tooth is suitably shaped for adherence of the virtual dental attachment thereto.

9. A method of forming dental appliances based on virtually testing force placed on a virtual tooth, the method comprising:
  receiving a desired position of a tooth of a patient included in initial orthodontic data (IOD), wherein the IOD includes tooth data of the patient;
  determining at least one of a desired force and torque to be applied to the virtual tooth such that the virtual tooth moves from an initial position to the desired position;
  determining a placement area on the virtual tooth for a virtual dental attachment to achieve a result within a threshold proximity to at least one of the desired force and torque applied to the virtual tooth in response to interaction between a virtual aligner and the virtual dental attachment;
  determining an attachment location in the placement area on the virtual tooth for the virtual dental attachment;
  displaying, via a user interface, the virtual dental attachment at the attachment location on the virtual tooth;
  receiving instructions from a user to place the virtual dental attachment at a first attachment location in the placement area on the virtual tooth to determine a first at least one force and torque applied to the virtual tooth;
  receiving instructions from the user to place the virtual dental attachment at a second attachment location in the placement area to determine a second at least one force and torque applied to the virtual tooth;
  determining a final attachment location by determining which of the first and second at least one force and torque applied to the virtual tooth is closer to the at least one of the desired force and torque to move the virtual tooth from the initial position to the desired position; and
  forming an aligner and a dental attachment shaped in accordance with the virtual aligner and virtual dental attachment, the aligner and the dental attachment shaped to cooperate together to apply the at least one of the desired force and torque to the tooth of the patient when the dental attachment is positioned at the final attachment location on the tooth of the patient.

10. The method of claim 1, further comprising receiving instructions from the user to adjust a shape of the virtual dental attachment.

11. The method of claim 1, further comprising displaying at least one of the desired force and force movement on the tooth as vector arrows, wherein the vector arrows indicate at least one of a direction and magnitude of the desired force.

12. The method of claim 1, further comprising receiving instructions from the user to adjust an orientation of the virtual dental attachment.

* * * * *